United States Patent [19]

Berlin

[11] Patent Number: 4,925,391
[45] Date of Patent: May 15, 1990

[54] DENTAL INSTRUMENT

[76] Inventor: Göran Berlin, Strandvägen 28, S-198 00 Bålsta, Sweden

[21] Appl. No.: 934,411
[22] PCT Filed: Mar. 4, 1986
[86] PCT No.: PCT/SE86/00092
§ 371 Date: Nov. 4, 1986
§ 102(e) Date: Nov. 4, 1986
[87] PCT Pub. No.: WO86/05086
PCT Pub. Date: Sep. 12, 1986

[30] Foreign Application Priority Data

Mar. 7, 1985 [SE] Sweden .............................. 85011237

[51] Int. Cl.⁵ .................................................. A61C 3/00
[52] U.S. Cl. ....................................................... 433/31
[58] Field of Search .................................... 433/30, 31

[56] References Cited

U.S. PATENT DOCUMENTS

| | | | |
|---|---|---|---|
| 1,905,633 | 4/1933 | Feltham | 433/30 |
| 1,925,981 | 9/1933 | Hopkins | 433/31 |
| 2,984,909 | 5/1961 | Johnston | 433/30 |
| 3,001,288 | 9/1961 | Freedman | 433/31 |
| 3,052,031 | 9/1962 | Piscitelli | 433/30 |
| 3,092,910 | 6/1963 | Warriner | 433/31 |
| 3,118,231 | 1/1964 | Rathsmill | 433/31 |
| 3,256,603 | 6/1966 | White | 433/31 |
| 3,928,916 | 12/1975 | Hansson | 433/31 |
| 4,386,910 | 6/1983 | Cattani | 433/92 |

FOREIGN PATENT DOCUMENTS 1580040 11/1980 United Kingdom ................. 433/31

Primary Examiner—John Weiss
Assistant Examiner—Adriene J. Lepiane
Attorney, Agent, or Firm—Nies, Kurz, Bergert & Tamburro

[57] ABSTRACT

A dental instrument including a shaft having firmly attached at one end thereof a mirror which is carried by a housing provided with an inlet opening to a first internal channel which communicates with a channel provided in the shaft, this latter channel being intended for connection to a suction source. According to the invention the shaft (17) incorporates a second channel (16) having one end which opens above the mirror (2) and the other end of which is intended for connection to a pressurized-air source via a control means (23) effective to regulate the supply of pressurized air to a turbine drill, whereby the supply of pressurized air to the instrument (1) is proportional to the supply of pressurized air to the turbine drill, and whereby the pressurized air supplied to the instrument (1) is blown over the mirror (2).

4 Claims, 2 Drawing Sheets

DENTAL INSTRUMENT

The present invention relates to a dental instrument.

When examining and treating the teeth of a dental patient, it is often necessary to place a suction device in the patient's mouth in order to remove saliva therefrom.

In present day dental surgeries, teeth are normally drilled with the aid of a drill which drives a drill bit by means of a turbine. A drill of this kind is provided with water jets or nozzles located in the vicinity of the drill bit. Significant quantities of water are sprayed through the jets onto the teeth in order to cool the teeth while drilling takes place. Fragments of the tooth being drilled, together with old fillings when found, are loosened and broken away during drilling of the teeth.

In order for the dentist to be able to drill a tooth properly, he/she must be able to see the drilling site clearly. Consequently, it is necessary to remove continuously all saliva, water, tooth and filling debris from around the tooth, so that the drilling site is kept clean.

To this end there is used a suction device in the form of a straight pipe, normally a plastics pipe, which is connected to a suction source by means of a connecting hose.

In order to be able to see the drilling site clearly, and to illuminate the drilling site, there is used a dental mirror by means of which light is reflected from an overhead lamp onto the drilling site.

Thus, it is often necessary for the dentist to use a drill, a suction device and a mirror simultaneously, at one and the same time. In addition to being extremely difficult, if not impossible, to hold all three instruments at the same time, a further problem resides in the fact that access to the tooth area decreases with the number of instruments placed in the location of the tooth.

In order to enable three instruments to be used simultaneously, the suction device is normally held in place by the dental nurse while the dentist holds the drill and the mirror.

Thus, it is necessary for the dental nurse to remain at the patient's side, together with the dentist, solely because of the need to use three instruments.

It has previously been proposed to combine a mirror with a suction device. This proposal, however, gives rise to a further problem, namely that the mirror, and therewith the suction device, must be frequently removed from the mouth cavity, in order to clean the mirror so that the working area can be seen clearly. Because of this the use of a conventional suction device and a conventional mirror prevails, despite the aforesaid disadvantages associated therewith.

The aforementioned problems are fully solved by means of the present invention, which provides an instrument which enables solely the instrument and a drill to be used simultaneously.

The present invention relates to a dental instrument comprising a shaft having firmly mounted on one end thereof a mirror which is supported by a housing provided with an inlet opening leading to a first internal channel which communicates with a further channel provided in the shaft, this channel being intended for connection to a suction source, and is characterized in that the shaft incorporates a second channel having one end which opens above the mirror and the other end of which is intended for connection to a pressurized-air source via a control means for controlling the supply of pressurized air to a turbine drill, whereby the supply of pressurized air to the instrument is proportional to the supply of pressurized air to said turbine drill, whereby the pressurized air supplied to the instrument is blown over the mirror. The invention will now be described in more detail with reference to the accompanying drawings, in which FIG. 1 is a sectional view of the instrument according to the invention;

Figure 1:
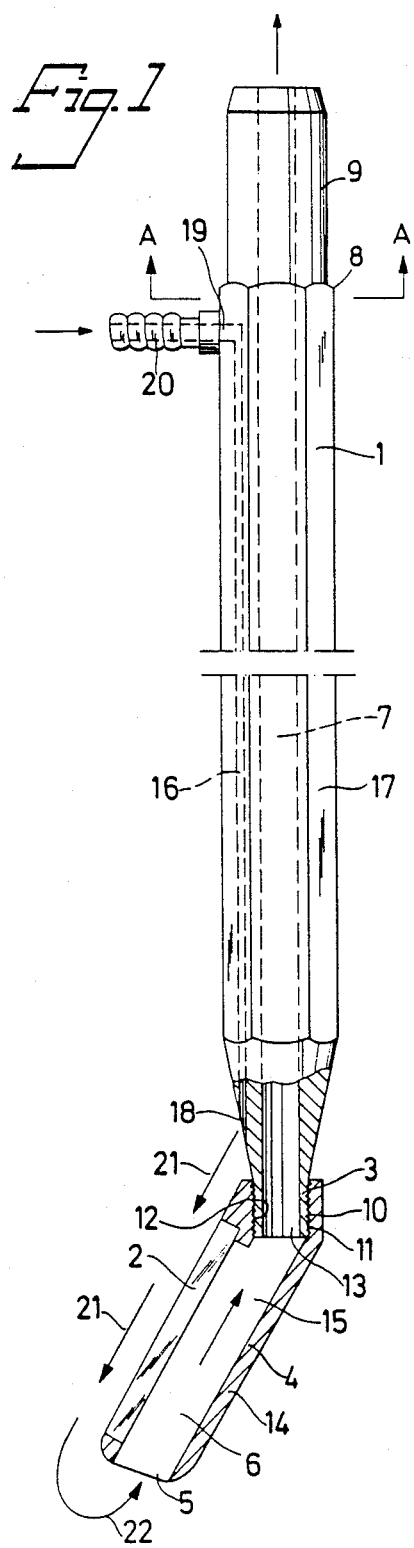
Figure 2:
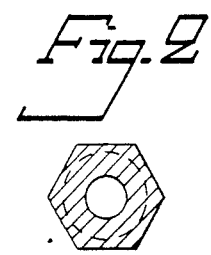
FIG. 2 is a sectional view taken on the line A—A in FIG. 1.

FIG. 5 is a schematic diagram illustrating coupling of the instrument. FIG. 1 illustrates a dental instrument 1 constructed in accordance with the invention and comprising a shaft 17 and a mirror 2 which is intended for attachment to the lower end 3 of the shaft. The mirror 2 is carried by a housing 4. The housing 4 is provided with an inlet opening 5 which leads to a first internal channel 6. When the housing 4 is mounted on the shaft, the internal channel 6 communicated with a channel 7 located in the shaft 1. The channel 7 located in the shaft is intended to be connected at the upper end 8 of said shaft to a suction source, via a hose suitably fitted onto a cylindrical section 9 provided at the upper end 8 of the shaft. The shaft 17 is of hexagonal cross-section along the major part of its length, as illustrated in FIG. 1, thereby to enable the shaft to be gripped more comfortably.

The lower end 3 of the shaft has the form of a pipe connector 10 which constitutes the mouth of the channel 7. The pipe connector 10 is provided with external screw-threads 11, which co-act with internal screw-threads 12 provided in the upper mouth or orifice 13 of the channel 6 in the housing 2, when the housing is attached to the shaft. The housing 2 is thus removably connected to the shaft 17, which can be beneficial from a cleaning aspect.

The shaft is made from metal or of plastics material.

Figure 3:
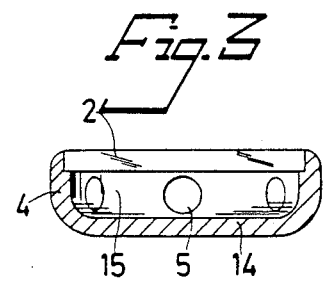
FIG. 3 is a sectional view taken on the line B—B in FIG. 4.
Figure 4:
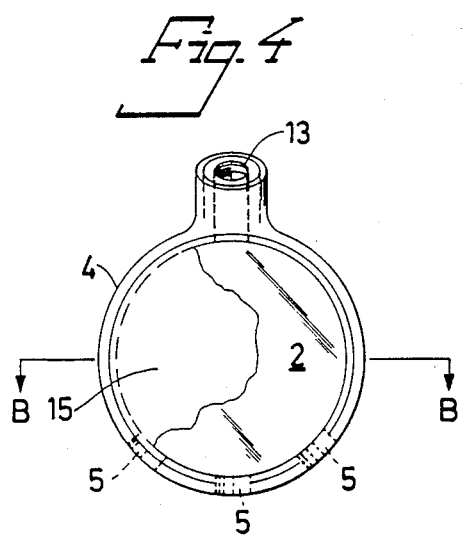
FIG. 4 is a plan view of the mirror.
Figure 6:
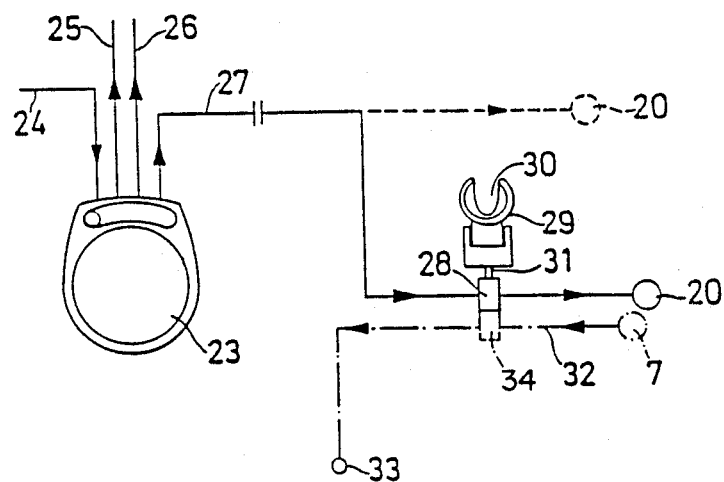

In accordance with one embodiment of the invention illustrated in FIGS. 1 and 3, the housing 1 comprises a bowl-shaped part 14 which is covered by the mirror 2. The bowl-shaped portion 14 may be made of metal or a plastics material. The mirror 2 may either be made of glass or metal. In accordance with this embodiment, the internal channel 6 of the housing comprises an inner cavity 15, to which one or more inlet openings 5 are found in the part of the housing 4 distal from the shaft 1.

In use the instrument functions both as a mirror and as a suction device. Saliva together with tooth and filling residues are removed by suction through the inlet openings 5 and the channels 6, 7, away from the region of the tooth being treated.

It will be understood that the housing and the mirror, and also the shaft, can be given other forms than those illustrated and described, without departing from the concept of the invention. For example, an instrument comprising mirror and suction device can be combined in one and the same instrument assembly, with the inlet openings located in the vicinity of the mirror.

In accordance with the invention a second channel 16 is provided in the shaft 17. The one end 18 of the further channel 16 opens in the shaft at a location above the mirror 2, whereas the other end 19 of the channel 16 is intended to be connected to a source of pressurized-air. The other end 19 of the channel preferably terminates in a nipple 20, onto which a hose extending from the pressurized-air source can be fitted. When pressurized-air is forced through the channel 16, air will be blown over the mirror 2, as indicated by the arrows 21, thereby keeping the mirror 2 clean. Because air is sucked into the housing through the inlet openings 5 and along the channel 7 in the shaft, part of the airstream 21 will oscillate around the lower end of the mirror, as indicate by the arrow 22, therewith contributing in maintaining a sweeping airflow over the mirror.

The instrument according to the invention is also intended for connection to the pressurized-air output line of a control means for controlling pressurized air to one or more pressurized-air driven turbine drills.

One such control means is referenced 23 in FIG. 5. The control means has connected thereto a pressurized-air supply line 24, and has extending therefrom a number of pressurized-air lines 25, 26, leading to one or more drills. In accordance with the invention, an additional pressurized-air line 27 departs from the control means. This pressurized-air line 27 can also be connected to one of the aforesaid outgoing lines 25, 26. The pressurized-air line 27 is connected to the nipple 20. According to one embodiment, the pressurized-air line 27 is connected directly to the nipple 20, as indicated in broken lines in FIG. 5. According to another embodiment, the pressurized-air line 27 is connected to the nipple 20 via a valve 28. The valve 28 is controlled by means of an instrument holder 29 of the kind used for turbine drills. When an instrument is placed in the upper part 30 of the holder, a shaft 31 is activated so as to close the valve 28. When an instrument is lifted from the holder, on the other hand, the valve 28 opens.

As a result of this connection of the present instrument, the amount of air supplied to the instrument will be proportional to the amount of air which the control means allows to pass through for the turbine drill. The control means is normally regulated by means of a foot pedal.

When drilling a tooth, the amount of tooth substance filling etc. removed from the tooth increases with the speed of the drill. In addition, the amount of water exiting from the water ducts or channels in the drill head also increases with increasing drill speeds. Thus, the amount of air which flows 21 across the mirror 2 via the channel 6 will be proportional to the drill speed.

It has been found that a particularly valuable advantage is afforded when the air stream 21 over the mirror increases when the drill speed increases. This enables the mirror to be kept constantly clean and clear, thereby enabling the dentist to see the drilling site clearly. Another important advantage afforded by the described arrangement used to connect the instrument resides in the ability of continuously varying the air flow by means of said control means when the instrument is used to syringe the teeth. Syringing of the teeth can be effected by distancing the instrument from the working site and thereafter regulating the air flow to the instrument with the aid of the aforesaid foot pedal. Thus, it is not necessary for the dentist to hang-up the drill and then take a conventional prophylactic instrument to syringe the teeth, and then hang-up the syringe and again take-up the drill. Thus, syringing of the teeth, which is normally required during drilling work, can be effected to advantage with the aid of the present instrument. Conventional tooth-syringes, however, are required for other prophylactic purposes.

When it is found necessary to add water during drilling of a tooth, it has been found a simple and effective expedient to ease the drill bit from the drilling site and to firstly direct the mouth 18 of the channel 16 towards the working site and secondly to direct the mouth of the water channels of the drill head towards said working site, and then to increase the air flow to the instrument, with the aid of the aforesaid foot pedal, such that water from the drill head is mixed with the air exiting from the present invention.

Thus, all the factors required to carry out a drilling operation namely drill, mirror, suction device, water and pressurized air are found available solely in two instruments. The instrument thus enables a dentist to treat a patient completely alone, in those cases where a suction device, a mirror and a drill need to be used simultaneously, thus dispensing with the presence of a dental nurse. In addition, the instrument increases the available access to the tooth in question, since no separate suction device is required.

It will also be perceived that fewer manual manipulations are required when working with an instrument constructed in accordance with the present invention.

The use of an instrument holder 29 for the present instrument affords the advantage that the supply of oxygen to the instrument is cut-off when the instrument is placed in the receiver 30 of holder 29.

According to one preferred embodiment, the instrument holder via its support member 31 is connected to a further valve 34 for closing and opening a suction line 32 connected at one end to a suction source 33 and at its other end to the suction channel 7 in the instrument.

The present invention is not restricted to the aforedescribed embodiments, and modifications can be made within the scope of the following claims.

I claim:

1. A dental instrument combined with a control wherein said dental instrument comprises: a shaft with two ends, a mirror having an upper and a lower surface, and a mirror housing firmly mounted on one end of said shaft, said housing being bowl-shaped and having an upper peripheral portion which encircles and receives said mirror so that no part of said housing distal from said shaft projects above the upper surface of said mirror, a portion of said bowl-shaped housing spaced from the shaft and disposed below the lower surface of the mirror is provided with at least one inlet opening, an internal channel provided through said housing under said mirror in fluid communication with said at least one inlet opening and in fluid communication with a first shaft channel located in the shaft, said first shaft channel being provided with means enabling connection to a suction source, characterized in that: said shaft (17) incorporates a second shaft channel (16) having two ends, one end of which opens from adjacent said one end of the shaft above said mirror to cause an air jet to be directed toward a tooth to cause an air syringe effect on the tooth as well as an air flow toward, over and past said mirror (2) and said upper peripheral distal portion of said mirror housing, and the other end of said second shaft channel (16) opens from the shaft at a location remote from said mirror; said control including an instrument holder (29) comprising a single control means connected to a source of pressurized air and having pressurized air outlet lines, one of which outlet lines is adapted to be connected to a turbine drill and another of which outlet lines (27) connects to the other end of said second shaft channel, whereby said single control means (23) simultaneously regulates the supply of pressurized air to said dental instrument and to a turbine drill, so that the supply of pressurized air to the instrument (1) is proportional to the supply of pressurized air to the turbine drill, and whereby the supply of pressurized air supplied to the instrument (1) is blown over the mirror (2), and said control further includes a suction control valve (34) connected to said instrument holder (29), a suction source connected to the outlet side of said suction control valve (34) and a suction line (32) connected between the inlet of said valve (34) and the said means in said first shaft channel which enables connection to a suction source; said valve (34) being closed when the instrument (1) is located in the holder (29) and open when said instrument is removed from said holder.

2. A dental instrument according to claim 1, characterized in that the said internal channel of the housing (4) is formed by an inner cavity (15) to which said at least one inlet opening (5) is found in said portion of the housing (4) distal from the shaft (17).

3. A dental instrument according to claim 1, characterized in said one end (3) of the shaft (17) has the form of a pipe connector (10) forming a mouth of said first channel (7) in the shaft (17), the housing (4) being removably attached to the pipe connector (10).

4. A dental instrument according to claim 1, characterized in that said single control means includes an air pressure control valve (28), said line (27) for supplying pressurized air to the instrument (1) extends from said air pressure control valve (28) which is for closing and opening the aforesaid air pressure supply line, said air pressure control valve being connected to and controlled by said holder whereby the air pressure control valve is closed when the dental instrument is located in the holder and said air pressure control valve is open when the dental instrument is removed form the holder.

* * * * *

UNITED STATES PATENT AND TRADEMARK OFFICE
CERTIFICATE OF CORRECTION

PATENT NO. : 4,925,391

DATED : May 15, 1990

INVENTOR(S) : GÖRAN BERLIN

It is certified that error appears in the above-identified patent and that said Letters Patent is hereby corrected as shown below:

IN THE SPECIFICATION:

Column 2, line 15, "FIG. 1" should be the beginning of a paragraph.

Column 2, line 22, "communicated" should read --communicates--.

IN THE CLAIMS:

Claim 3, column 6, line 4, insert "that" after --in--.

Signed and Sealed this

Twentieth Day of August, 1991

Attest:

HARRY F. MANBECK, JR.

*Attesting Officer*  *Commissioner of Patents and Trademarks*